US00PP23044P2

(12) United States Plant Patent
Conibear

(10) Patent No.: US PP23,044 P2
(45) Date of Patent: Sep. 18, 2012

(54) LUPINE PLANT NAMED 'TERRACOTTA'

(50) Latin Name: ***Lupinus* hybrid**
Varietal Denomination: Terracotta

(75) Inventor: Sarah Frances Conibear, Bideford (GB)

(73) Assignee: Specialis Plants BV, Oude Wetering (NL)

( * ) Notice: Subject to any disclaimer, the term of this patent is extended or adjusted under 35 U.S.C. 154(b) by 0 days.

(21) Appl. No.: 13/134,176

(22) Filed: May 31, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — C. A. Whealy

(57) ABSTRACT

A new and distinct cultivar of Lupine plant named 'Terracotta', characterized by its upright plant habit; vigorous growth habit; numerous large orange red-colored flowers arranged on dense terminal racemes; and good garden performance.

2 Drawing Sheets

Botanical designation: *Lupinus* hybrid.
Cultivar denomination: 'TERRACOTTA'.

BACKGROUND OF THE INVENTION

The present invention relates to a new and distinct cultivar of Lupine plant, botanically known as *Lupinus* hybrid and hereinafter referred to by the name 'Terracotta'.

The new Lupine plant is a product of a planned breeding program conducted by the Inventor in Devon, United Kingdom. The objective of the breeding program is to develop new uniform and freely flowering Lupine plants with large attractive flowers.

The new Lupine plant originated from an open-pollination in June, 2005 of a seedling selection of *Lupinus* hybrid identified as *Lupinus* Russell Hybrid Seedling WCL 024/62, not patented, as the female, or seed, parent with an unknown selection of *Lupinus* hybrid as the male, or pollen, parent. The new Lupine plant was discovered and selected by the Inventor in June, 2006 as a single flowering plant within the progeny of the stated open-pollination in a controlled environment in Devon, United Kingdom.

Asexual reproduction of the new Lupine plant by micro propagation in a controlled greenhouse environment in Hillegom, The Netherlands since March, 2009 has shown that the unique features of this new Lupine plant are stable and reproduced true to type in successive generations of asexual reproduction.

SUMMARY OF THE INVENTION

Plants of the new Lupine have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Terracotta'. These characteristics in combination distinguish 'Terracotta' as a new and distinct Lupine plant:

1. Upright plant habit.
2. Vigorous growth habit.

3. Numerous large orange red-colored flowers arranged on dense terminal racemes.
4. Good garden performance.

Plants of the new Lupine can be compared to plants of the female parent selection. Plants of the new Lupine differ from plants of the female parent selection primarily in plant growth habit and flower color.

Plants of the new Lupine can be compared to plants of *Lupinus* hybrid 'Manhattan Lights', disclosed in U.S. Plant Pat. No. 18,868. Plants of the new Lupine differ from plants of 'Manhattan Lights' in the following characteristics:

1. Plants of the new Lupine are shorter than plants of 'Manhattan Lights'.
2. Plants of the new Lupine and 'Manhattan Lights' differ in flower color as plants of 'Manhattan Lights' have burgundy and yellow-colored flowers.

Plants of the new Lupine can also be compared to plants of *Lupinus* hybrid 'Saffron', disclosed in U.S. Plant Pat. No. 18,802. Plants of the new Lupine differ from plants of 'Saffron' in the following characteristics:

1. Plants of the new Lupine are taller than plants of 'Saffron'.
2. Plants of the new Lupine and 'Saffron' differ in flower color as plants of 'Saffron' have yellow-colored flowers.

BRIEF DESCRIPTION OF THE PHOTOGRAPHS

The accompanying colored photographs illustrate the overall appearance of the new Lupine plant showing the colors as true as it is reasonably possible to obtain in colored reproductions of this type. Colors in the photographs may differ slightly from the color values cited in the detailed botanical description which accurately describe the colors of the new Lupine plant.

The photograph on the first sheet is a close-up view of a typical flowering plant of 'Desert Sun' grown in a container.

The photograph at the top of the second sheet is a side perspective view of a typical flowering plant of 'Desert Sun' grown in a container.

The photograph at the bottom of the second sheet is a close-up view of a typical leaf of 'Desert Sun'.

DETAILED BOTANICAL DESCRIPTION

The aforementioned photographs and following observations, measurements and values describe plants of the new Lupine grown during the early summer in 3-liter containers in an outdoor nursery in Vogelenzang, The Netherlands and under cultural practices which closely approximate commercial Lupine production. During the production of the plants, day temperatures ranged from 16° C. to 26° C. and night temperatures ranged from 6° C. to 16° C. Plants were one year old when the photographs and the detailed description were taken. In the detailed description, color references are made to The Royal Horticultural Society Colour Chart, 2007 Edition, except where general terms of ordinary dictionary significance are used.

Botanical classification: *Lupinus* hybrid 'Terracotta'.

Parentage:

*Female, or seed, parent.*—*Lupinus* Russell Hybrid Seedling WCL 024/62, not patented.

*Male, or pollen, parent.*—Unknown selection of *Lupinus* hybrid, not patented.

Propagation:

*Type.*—By micro propagation.

*Time to initiate roots.*—About four to five days at 20° C.

*Time to produce a rooted young plant, summer.*—About five to six weeks at 15° C. to 17° C.

*Time to produce a rooted young plant, winter.*—About seven to eight weeks at 15° C. to 17° C.

*Root description.*—Thick, fleshy; creamy white to light brown in color.

*Rooting habit.*—Main tap root with low lateral branching; medium in density.

Plant description:

*Plant and growth habit.*—Upright plant habit; vigorous growth habit.

*Branching habit.*—Freely basal branching habit.

*Plant height.*—About 57.2 cm.

*Plant diameter* (*area of spread*).—About 49.1 cm.

Lateral branch description:

*Length.*—About 18.1 cm.

*Diameter.*—About 1.3 cm.

*Internode length.*—About 1.8 cm.

*Texture.*—Densely pubescent.

*Strength.*—Strong.

*Color.*—Between 144B and 146C.

Foliage description:

*Arrangement.*—Alternate, palmately compound with about twelve leaflets per leaf.

*Leaf length.*—About 17.9 cm.

*Leaf width.*—About 17.9 cm.

*Leaflet length.*—About 10.8 cm.

*Leaflet width.*—About 2.7 cm.

*Leaf shape.*—Orbicular.

*Leaflet shape.*—Oblanceolate.

*Leaflet apex.*—Broadly acute.

*Leaflet base.*—Cuneate.

*Leaflet margin.*—Entire.

*Leaflet texture, upper surface.*—Smooth, glabrous.

*Leaflet texture, lower surface.*—Sparsely pubescent.

*Leaflet venation pattern.*—Pinnate.

*Leaflet color.*—Developing leaflets, upper surface: Close to 143A to 143B. Developing leaflets, lower surface: Close to 139C. Fully expanded leaflets, upper surface: Close to N137D; venation, close to 144A to 144B. Fully expanded leaflets, lower surface: Close to 138A; venation, close to 138A to 138B.

*Leaf petiole.*—Length: About 19.5 cm. Diameter: About 4 mm. Texture, upper and lower surfaces: Smooth, glabrous. Color, upper and lower surfaces: Close to 144A; upper leaves tinged with close to 183C.

Flower description:

*Flower appearance/arrangement.*—Single large papilionaceous flowers arranged in dense racemes; freely flowering habit with usually about 250 flowers developing per inflorescence; flowers face mostly outwardly.

*Natural flowering season.*—Continuous flowering from late spring through the summer in The Netherlands.

*Flower longevity.*—Flowers last about two weeks on the plant; flowers not persistent.

*Fragrance.*—Moderately fragrant; pleasant and sweet.

*Inflorescence height.*—About 39.8 cm.

*Inflorescence diameter.*—About 7.8 cm.

*Flower diameter.*—About 2.1 cm by 2.2 cm.

*Flower length* (*height*).—About 2.4 cm.

*Flower buds.*—Length: About 7 mm. Diameter: About 5 mm. Shape: Ovate. Color: Close to 186A; calyx, close to 145C.

*Petals.*—Quantity per flower: Flowers papilionaceous with an upper standard petal, two lateral petals and a lower keel of two united petals. Length: Upper standard petal: About 2.1 cm. Lateral petals: About 2.2 cm. Lower keel: About 1.6 cm. Width: Upper standard petal: About 1.9 cm. Lateral petals: About 1.7 cm. Lower keel: About 1 cm. Shape: Upper standard petal: Orbicular; convex. Lateral petals: Obovate; curved and concave. Lower keel: Ovate; curved and folded. Apex: Upper standard petal: Emarginate. Lateral petals: Rounded. Lower keel: Caudate. Margin, all petals: Entire. Texture, upper and lower surfaces, all petals: Smooth, glabrous. Color, when opening, upper surface: Upper standard petal: Close to 59D; central blotch, close to 26B. Lateral petals: Close to 49B. Lower keel: Close to 150D; apex, close to N199B. Color, when opening, lower surface: Upper standard petal: Close to 59D; central blotch, close to 26B. Lateral petals: Close to 48C. Lower keel: Close to 150D; apex, close to N199B. Color, fully opened, upper surface: Upper standard petal: Close to 48B; central blotch, close to 14B; base of central blotch, dots, close to 203D; with development, ground color becoming closer to 35C and central blotch becoming closer to 13B. Lateral petals: Close to 34D; with development, color becoming closer to 35B and towards the base, close to 29C. Lower keel: Close to 150D; apex, close to N199B; color does not change with development. Color, fully opened, lower surface: Upper standard petal: Close to 48A; central blotch, close to 13B; with development, ground color becoming closer to 35C. Lateral petals: Close to N34D; with development, color becoming closer to 35B and towards the base, close to 29C. Lower keel: Close to 150D; apex, close to N199B; color does not change with development.

*Sepals.*—Quantity per flower: Two. Length: About 7 mm. Width: About 6 mm. Shape: Ovate. Apex: Acute. Base: Cuneate. Margin: Entire. Texture, upper and lower surfaces: Densely pubescent. Color, when opening, upper and lower surfaces: Close to 145C. Color, fully opened, upper and lower surfaces: Close to 145B.

*Peduncles*.—Length: About 39.5 cm. Diameter: About 9 mm. Strength: Strong. Aspect: Mostly erect. Texture: Smooth, glabrous. Color: Close to 183B.

*Pedicels*.—Length: About 1.1 cm. Diameter: About 1 mm. Strength: Moderately strong. Aspect: About 60° from peduncle axis. Texture: Smooth, glabrous. Color: Close to 182B to 182D.

*Reproductive organs*.—Androecium: Quantity per flower: About ten. Filament length: About 4 mm to 7 mm. Filament color: Close to 144B to 144C. Anther shape: Narrowly oblong. Anther length: About 2 mm. Anther color: Close to 169B to 169D. Amount of pollen: Moderate to abundant. Pollen color: Close to 24A. Gynoecium: Quantity per flower: One. Pistil length: About 1.3 cm. Style length: About 1.25 cm. Style color: Close to 150D. Stigma shaped: Club-shaped, fringed. Stigma color: Close to 145D. Ovary color: Close to 144C to 144D.

*Fruits*.—Quantity per flower: One. Length: About 4.6 cm. Diameter: About 1 cm. Texture: Densely pubescent. Color: Close to 165A.

*Seeds*.—Quantity per fruit: About ten. Length: About 5 mm. Diameter: About 2 mm. Color: Close to 200A.

Garden performance: Plants of the new Lupine have been observed to have good garden performance and to tolerate rain, wind, high temperatures of about 35° C. and to be hardy to USDA Hardiness Zone 5.

Pathogen & pest resistance: Plants of the new Lupine have not been observed to be resistant to pathogens and pests common to Lupine plants.

It is claimed:

1. A new and distinct Lupine plant named 'Terracotta' as illustrated and described.

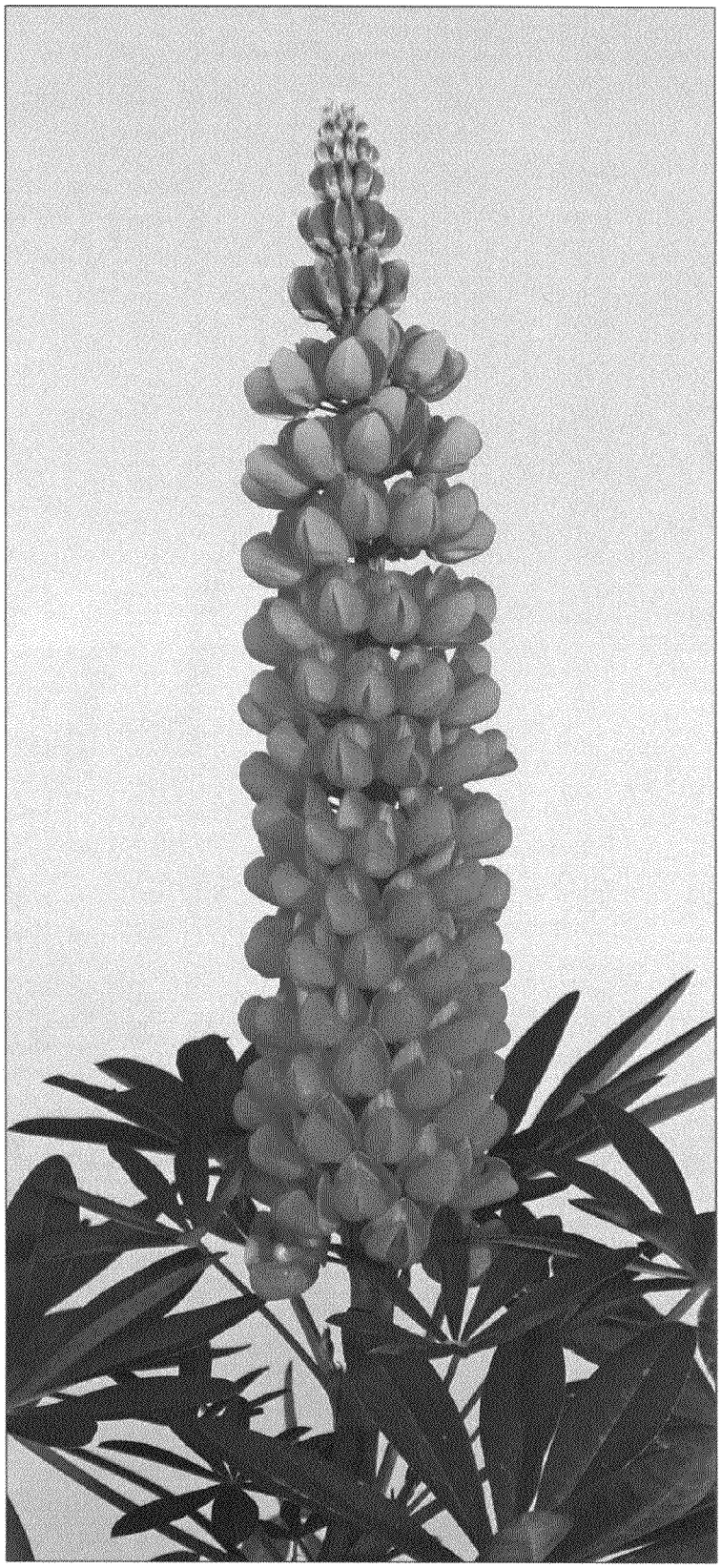

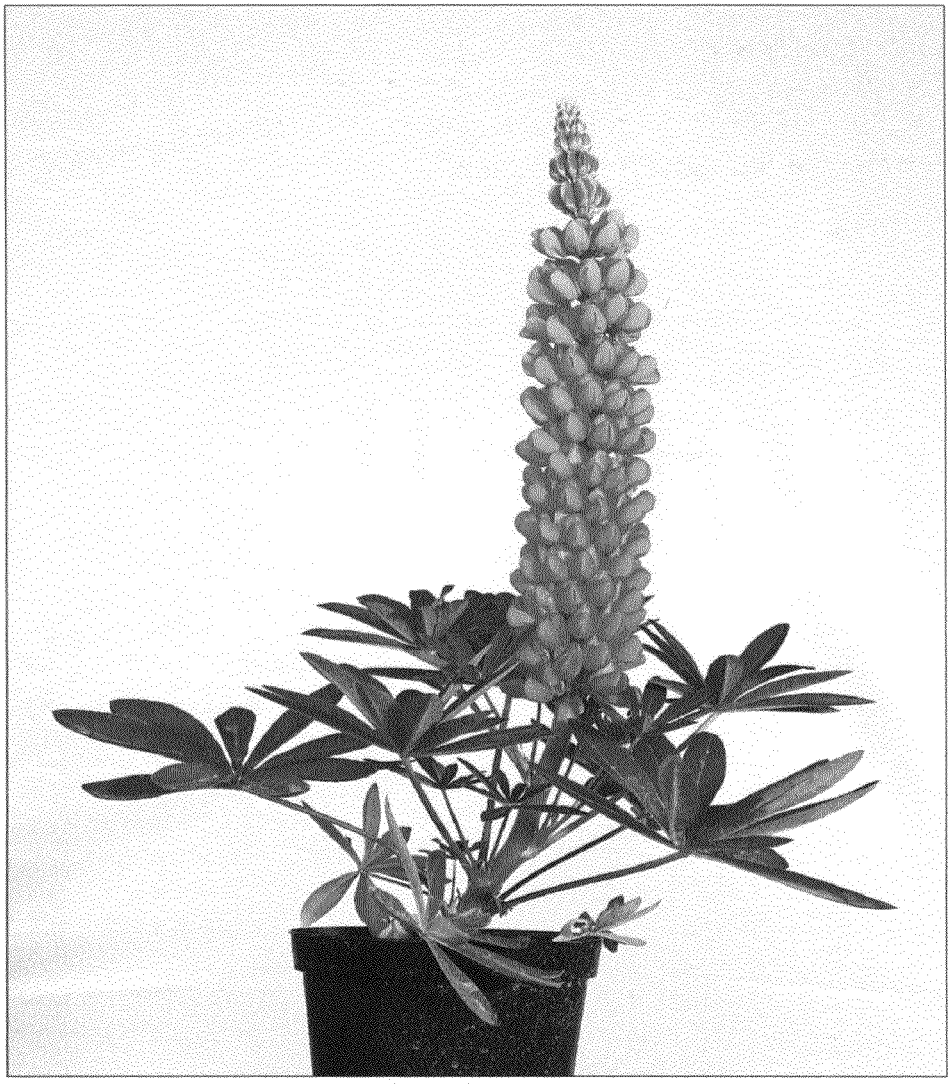
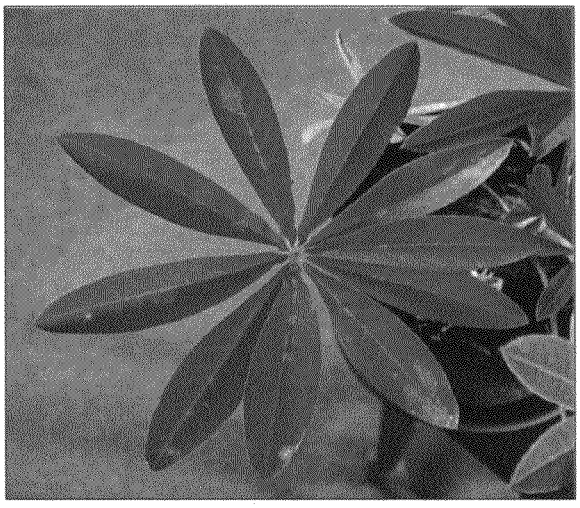

* * * * *